(12) United States Patent
Lee et al.

(10) Patent No.: US 6,600,065 B2
(45) Date of Patent: Jul. 29, 2003

(54) PROCESS FOR PREPARING 3-HYDROXYESTERS FROM EPOXIDE DERIVATIVES

(75) Inventors: Byeong No Lee, Daejun-Shi (KR); Eun Joo Jang, Daejun-Shi (KR); Hyung Soo Cho, Daegu-Shi (KR); Byung Soon Chun, Kyoungki-Do (KR)

(73) Assignee: Davy Process Technology Ltd., London (GB)

( * ) Notice: Subject to any disclaimer, the term of this patent is extended or adjusted under 35 U.S.C. 154(b) by 0 days.

(21) Appl. No.: 10/272,380

(22) Filed: Oct. 17, 2002

(65) Prior Publication Data

US 2003/0109744 A1 Jun. 12, 2003

(30) Foreign Application Priority Data

Oct. 17, 2001 (KR) ........................................ 2001-63986
Oct. 4, 2002 (KR) .................................... 2002-0060549

(51) Int. Cl.[7] .......................... C07C 69/66; C07C 69/76; C07C 69/00
(52) U.S. Cl. ............................. 560/179; 560/129; 560/8
(58) Field of Search .............................. 560/179, 8, 51, 560/121, 123, 126, 129, 114, 205, 209, 130, 174, 175

(56) References Cited

U.S. PATENT DOCUMENTS

| 4,973,741 | A | 11/1990 | Beavers |
| 5,310,948 | A | 5/1994 | Drent et al. |
| 5,359,081 | A | 10/1994 | Drent et al. |
| 5,723,389 | A | 3/1998 | Slaugh et al. |
| 5,731,478 | A | 3/1998 | Slaugh et al. |
| 5,770,776 | A | 6/1998 | Powell et al. |
| 5,981,808 | A | 11/1999 | Powell et al. |
| 5,986,145 | A | 11/1999 | Powell et al. |
| 6,191,321 | B1 | 2/2001 | Forschner et al. |

FOREIGN PATENT DOCUMENTS

KR 2001-1784 1/2001

*Primary Examiner*—Johann Richter
*Assistant Examiner*—Elvis O. Price
(74) *Attorney, Agent, or Firm*—Birch, Stewart, Kolasch & Birch, LLP

(57) ABSTRACT

Disclosed herein is a novel process for preparing 3-hydroxyesters, comprising: (a) reacting an epoxide derivative with carbon monoxide and alcohol in a solvent at a temperature of 30~150° C. under a pressure of 50~3000 psig by using a catalyst system consisting of a catalytic amount of a cobalt compound and optionally an effective amount of a promoter to produce a 3-hydroxyester or a derivative thereof; (b) separating the resulting product and the solvent from the cobalt compound and the promoter in a stripping column at a temperature of −30~200° C. in an atmosphere of a stabilizing gas; and (c) recycling a part or all of the separated cobalt compound and promoter to the step (a) and repeating the steps (a) through (c).

8 Claims, 3 Drawing Sheets

PROCESS FOR PREPARING 3-HYDROXYESTERS FROM EPOXIDE DERIVATIVES

This nonprovisional application claims priority under 35 U.S.C. §119(a) on patent application Ser. No. 2001-63986 and 2002-60549 filed in KOREA on Oct. 17, 2001 and Oct. 4, 2002, which is herein incorporated by reference.

FIELD OF THE INVENTION

The present invention relates to a process for preparing 3-hydroxyesters by carbonylating an epoxide derivative. More specifically, the present invention relates to converting an epoxide derivative into 3-hydroxyesters through reaction with carbon monoxide and alcohol in the presence of a catalyst system consisting of a cobalt catalyst and a promoter, followed by the efficient separation of the catalyst system from the resulting reaction product so as to recycle the catalyst system.

BACKGROUND OF THE INVENTION

Epoxide derivatives can be readily converted into a difunctional compound via carbonylation so that they can be used as an intermediate compound for preparing useful organic compounds. Particularly, since a 3-hydroxyester derivative has two functional groups, it has been known that it can be used as solvents, resins and coating materials. Further, it is possibly used as a raw material for pharmaceutical compounds or as an intermediate for organic synthesis due to its easy convertibility into other compounds and can also be used as an intermediate for synthesis of alkanediols, which are the raw material for polyesters. Such alkanediols, particularly 1,3-alkanediols have been generally prepared by hydroformylating an epoxide derivative into a 3-hydroxyaldehyde derivative and then hydrogenating the 3-hydroxyaldehyde derivative to convert aldehyde group thereof into alcohol group. This process is fully described in U.S. Pat. Nos. 5,770,776, 5,723,389 and 5,731,478 by Shell Co.

On the other hand, the preparation of 3-hydroxyaldehyde derivatives in a condition of relatively low temperature and low pressure with high selectivity has been accomplished by the use of a cobalt catalyst in conjunction with a promoter, a phosphine oxide ligand. However, this technique has been found to be troublesome in that the recovery and recycling of the catalyst is difficult in the presence of such promoter.

To solve these problems, U.S. Pat. No. 5,770,776 discloses a process for preparing 1,3-propandiol, comprising: contacting ethylene oxide with carbon monoxide and hydrogen in a non-aqueous solvent in the presence of a catalyst system consisting of a cobalt catalyst and an alternative promoter, i.e., a metal complex or a ligand other than the phosphine oxide ligand; adding an aqueous solution to the resulting intermediate product to obtain a first aqueous phase product and a first organic phase material; isolating the first aqueous phase product from the first organic phase material; adding a non-aqueous solvent to the first aqueous phase product to obtain a second aqueous phase product and a second organic phase material; isolating the second aqueous phase product from the second organic phase material; and recycling the first and the second organic phase materials to the first step, wherein the isolated second aqueous phase product containing 3-hydroxypropanal is contacted with hydrogen in the presence of a hydrogenation catalyst and the resulting 1,3-propandiol is finally recovered.

U.S. Pat. Nos. 5,723,389 and 5,731,478 disclose a process for preparing alkanediols, comprising: contacting ethylene oxide with carbon monoxide and hydrogen in the presence of a catalyst system consisting of a cobalt catalyst and an alternative promoter, i.e., a metal complex or a ligand other than the phosphine oxide ligand in a non-aqueous solvent; adding an aqueous solution to the resulting intermediate product to obtain an aqueous phase product and organic phase materials; isolating the aqueous phase product from the organic phase materials; contacting the aqueous phase product containing 3-hydroxyaldehyde with hydrogen in the presence of a hydrogenation catalyst, and recovering the resulting alkanediols.

U.S. Pat. Nos. 5,981,808 and 5,986,145 propose a process for preparing 1,3-propandiol, comprising contacting ethylene oxide with carbon monoxide and hydrogen in the presence of a catalyst system consisting of a cobalt catalyst and an alternative promoter, i.e., a metal complex or a ligand other than the phosphine oxide ligand in a non-aqueous solvent; adding an aqueous solution to the resulting intermediate product to obtain an aqueous phase product and an organic phase material; recycling the organic phase material to the first step, wherein the water-soluble cobalt catalyst is removed from the final reaction product, 3-hydroxypropanal, by contacting the aqueous phase product comprising 3-hydroxypropanal contaminated with the cobalt catalyst with oxygen or oxygen-containing gas(e.g., air) at 5~55° C. for 1~15 minutes in the presence of an adequate amount of organic acid under a pressure of 50~200 psig by carbon monoxide to convert the water-soluble cobalt catalyst into a water-insoluble cobalt compound, which in turn is removed out by using an ion-exchange resin. Nevertheless, the remaining aqueous phase has been found to include a considerable amount of cobalt in addition to 3-hydroxypropanal.

Meanwhile, U.S. Pat. No. 4,973,741 teaches that β-hydroxypropionate can be obtained by reacting carbon monoxide, hydrogen, ethylene oxide, and primary alcohol or benzyl alcohol together in the presence of a catalyst system consisting of rhodium and a promoter of Va family. However, this technique is also disadvantageous in that the yield of methyl 3-hydroxypropionate is only 66% in spite of the use of the expensive catalyst and a large amount of byproducts are produced.

According to another techniques, the conversion rate of an epoxide to a β-hydroxyester through hydroesterification has been reported to be only 40~60% (see: for example, Dalcanali, E., and Foa. M., Synthesis (1986) 492; Heck, R. F., J. Am. Chem. Soc. (1963) 85, 1460; and Eisenmann, J. L., Yamartino, R. L., Howard, Jr. J. F., J. Org. Chem. (1961) 26, 2102). It is surmised that such a low yield is due to the spontaneous isomerization of the starting material.

U.S. Pat. Nos. 5,310,948 and 5,359,081 disclose that a reaction of an epoxide with carbon monoxide up to 60 atm in the presence of a catalyst system consisting of cobalt and a pyridine derivative, particularly 3-hydroxypyridine, yielded primarily β-propiolactone, while 3-hydroxymethylpropionate may be produced according to the reaction condition. In these prior arts, however, there is no description on the recovery or recycling of the cobalt catalyst.

U.S. Pat. No. 6,191,321 describes a process for preparing 1,3-propandiol through the hydrogenation of 3-hydroxymethyl propionate. This technique also has a very low production yield and provides no description on the recovery and recycling of cobalt, which are merely supposed to be conducted in an aqueous phase.

In the preparation of 1,3-alkanediols, when 3-hydroxyaldehyde forms as an intermediate as in the prior arts, the inherent instability of the aldehyde causes the formation of oligomers as well as byproducts such as acetals, which consequently deteriorates quality of the final product. In addition, such complicated recovery and recycling of the cobalt catalyst remain to be solved.

As a part of effort to solve these problems with the prior arts, the present inventors already proposed a novel process for preparing 3-hydroxyesters and 1,3-alkanediols in Korean Patent Application No. 2001-1784. According to this technique, reaction product and catalyst are separated from each other by the vacuum distillation or the extraction of the catalyst into an aqueous phase, and the catalyst thus separated can be reused.

SUMMARY OF THE INVENTION

A feature of the present invention is to provide a novel process for preparing 3-hydroxyesters by reacting an epoxide derivative with carbon monoxide and alcohol in the presence of a catalyst system consisting of a cobalt catalyst and optionally a particular promoter to efficiently produce a 3-hydroxyester, followed by the isolation of the catalyst system form the reaction mixture in order to reuse it in another cycle of 3-hydroxyester preparation.

Another feature of the present invention is to provide a simplified technique for isolating the cobalt catalyst system without requiring intricate equipments or procedures, which allows minimum production cost to be incurred in the preparation of desired 3-hydroxyesters.

Still another feature of the present invention is to provide a novel process for preparing 3-hydroxyesters, comprising:

(a) reacting an epoxide derivative with carbon monoxide and alcohol in a solvent at a temperature of 30~150° C. under a pressure of 50~3000 psig by using a catalyst system consisting of a catalytic amount of a cobalt compound and optionally an effective amount of a promoter to produce a 3-hydroxyester or a derivative thereof;

(b) separating the resulting product and the solvent from the cobalt compound and the promoter in a stripping column at a temperature of −30~200° C. in an atmosphere of a stabilizing gas; and (c) recycling a part or all of the separated cobalt compound and promoter to the step (a) and repeating the steps (a) through (c).

Other feature and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The present invention will be more clearly understood by reference to the description which follows when taken together with the attached drawings in which.

DETAILED DESCRIPTION OF THE INVENTION

Figure 1:
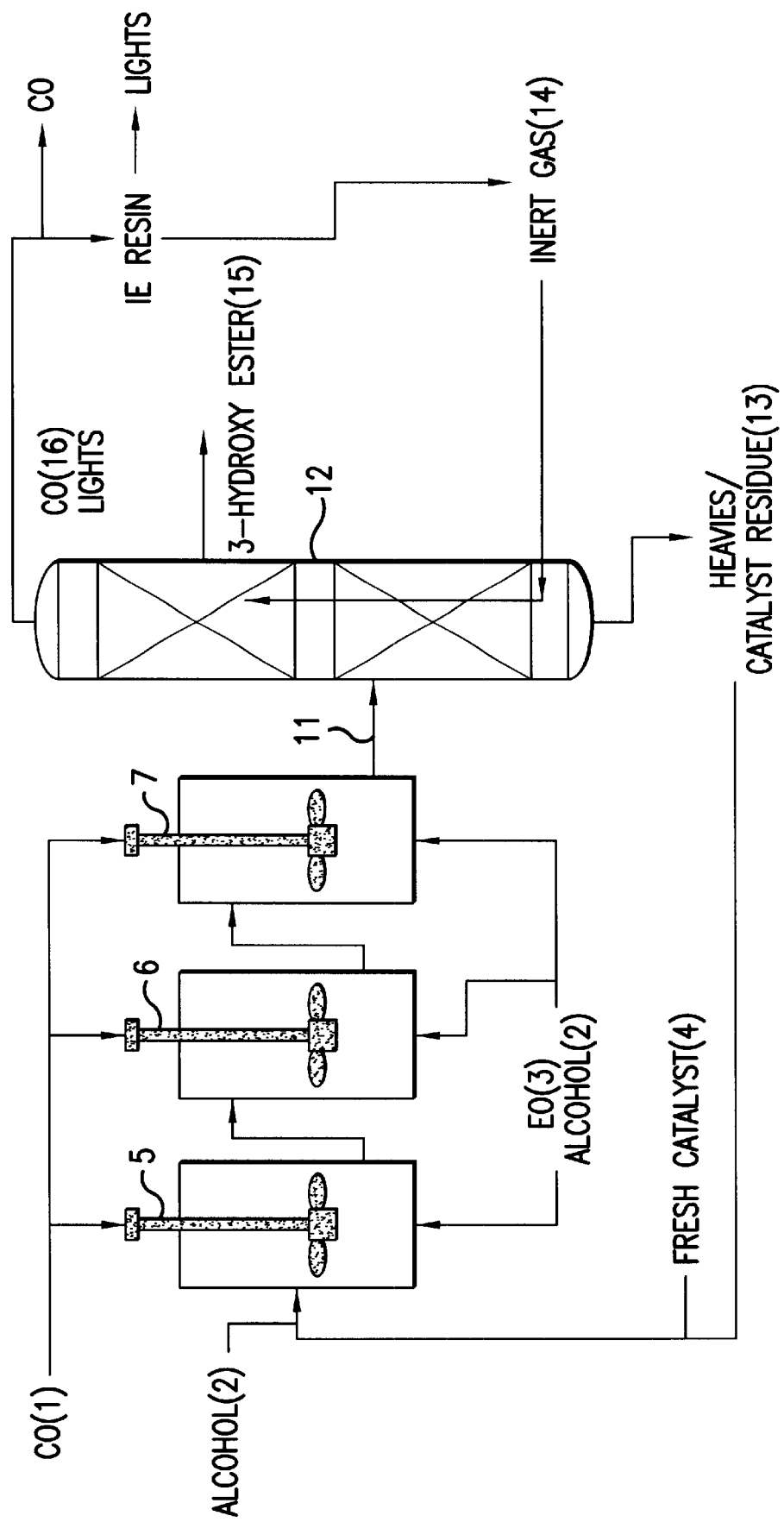
FIG. 1 is an outline reaction scheme illustrating a process for preparing 3-hydroxyesters from epoxide derivatives according to the present invention.

The present invention relates to a novel process for preparing 3-hydroxyesters through the carbonylation of an epoxide derivative in the presence of a catalyst system consisting of a cobalt compound and optionally a promoter, wherein the catalyst system can be successfully separated from the reaction product, 3-hydroxyesters, and then be reused in another cycle of such carbonylation. Thus, the present invention permits the production of 3-hydroxyesters with high efficiency at low cost by providing a progressive technique for recycling the catalyst consecutively.

As the catalyst system used in the carbonylation according to the present invention, a cobalt catalyst $Co_2(CO)_8$ can be used solely, or the cobalt catalyst $Co_2(CO)_8$ can be used in combination with a promoter selected from the group consisting of imidazole, pyridine, pyrrole, pyrazine, pyrazole, pyrimidine, piperidine and derivatives thereof, provided that the promoter does not comprise any phosphine-based compound. In the latter case, the cobalt compound is combined with the promoter so that the molar ratio of cobalt atom:promoter is 1:0~1:100(mol/mol). Particularly, the imidazole derivatives represented by the following Formula (I) are preferred as the promoter in consideration of their inexpensiveness:

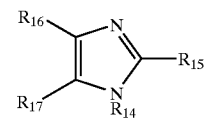

wherein, each of $R_{14}$, $R_{15}$, $R_{16}$ and $R_{17}$ is, independently, hydrogen; $C_{1-10}$ branched aliphatic hydrocarbon, non-branched aliphatic hydrocarbon, saturated cyclic hydrocarbon, chain-type hydrocarbon containing ring structure, or aliphatic hydrocarbon containing aromatic ring; F; Cl; $C_{1-3}$ alkoxy group; OH; or OH-containing $C_{1-10}$ branched aliphatic hydrocarbon, non-branched aliphatic hydrocarbon, saturated cyclic hydrocarbon, chain-type hydrocarbon containing ring structure, or aliphatic hydrocarbon containing aromatic ring.

In the present invention, the carbonylation is conducted in the presence of an talcohol by using an additional reaction solvent at a temperature of 30~150° C., preferably 40~120° C. under a pressure of 50~3000 psig, preferably 100~1500 psig by CO gas.

The epoxide derivatives used in the carbonylation are represented by the following Formula (II):

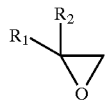

wherein,
each of $R_1$ and $R_2$ is, independently, hydrogen; $C_{1-20}$ saturated non-branched aliphatic hydrocarbon, branched aliphatic hydrocarbon, saturated cyclic hydrocarbon, chain-type hydrocarbon containing ring structure, or aliphatic hydrocarbon containing aromatic ring; hydrocarbon formed by substitution of at least one hydrogen in at least one carbon chain of the above hydrocarbon species with F, Cl or Br; unsubstituted aromatic hydrocarbon; or aromatic hydrocarbon formed by substitution of at least one hydrogen in the aromatic ring with F, Cl, amine, nitrile or alkoxy group.

Preferred examples of such epoxide derivatives include ethylene oxide, propylene oxide, 1-butene oxide, 1-pentene oxide, 1-hexene oxide, 1-heptene oxide, 1-octene oxide, 1-nonene oxide, 1-decene oxide, 2-methyl-propylene oxide, epifluorohydrin, epichlorohydrin, epibromohydrin, glycidol, methyl glycidate, ethyl glycidate, t-butyl glycidate, 2-methyl-1-butene oxide, 2-methyl-1-pentene oxide, 2-methyl-1-hexene oxide, 2-methyl-1-heptene oxide, 2-methyl-1-octene oxide, 2-methyl-nonene oxide, 2-methyl-1-decene oxide, 2-ethyl-1-butene oxide, 2-ethyl-1-pentene oxide, 2-ethyl-1-hexene oxide, 2-ethyl-1-heptene oxide, 2-ethyl-1-octene oxide, 2-ethyl-1-nonene oxide, 2-ethyl-1-decene oxide, allyl benzene oxide, and styrene oxide.

The alcohols used in the carbonylation can be represented by the Formula R'OH, wherein R' is $C_{1-20}$ saturated or unsaturated linear hydrocarbon, branched hydrocarbon, cyclic hydrocarbon, aromatic hydrocarbon or linear hydrocarbon containing aromatic ring. Preferably, R' is methyl, ethyl, isopropyl, cyclohexyl, phenyl or benzyl.

With regard to the solvent for the carbonylation, the R'OH itself can be used solely, or alternatively, ether compounds, substituted aromatic compounds, acetate compounds or carbonate compounds can be additionally used.

The ether compounds have the structure represented by the following Formulas (III), (IV), (V) or (VI):

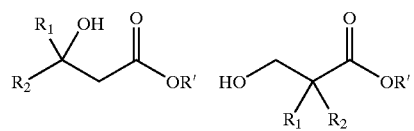

wherein,
each of $R_3$, $R_4$, $R_5$, $R_6$ and $R_7$ is, independently, $C_{1-10}$ saturated non-branched aliphatic hydrocarbon, branched aliphatic hydrocarbon, saturated cyclic hydrocarbon, chain-type hydrocarbon containing ring structure, or aliphatic hydrocarbon containing aromatic ring; m is an integer of 1 to 10; n is an integer of 2 to 5; and each of x and y is, independently, an integer of 1 to 10.

The substituted aromatic compounds can be exemplified by those represented by the following Formula (VII):

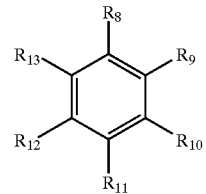

wherein,
each of $R_8$, $R_9$, $R_{10}$, $R_{11}$, $R_{12}$ and $R_{13}$ is, independently, hydrogen; $C_{1-4}$ saturated branched hydrocarbon; saturated non-branched hydrocarbon; F; Cl; or $C_{1-3}$ alkoxy group.

The acetate compounds and the carbonate compounds are not specifically limited, while preferred examples of the acetate compound include methyl acetate, ethyl acetate, propyl acetate, butyl acetate, and isopropyl acetate, and preferred examples of the carbonate compound include methyl carbonate, ethyl carbonate, propyl carbonate, and butyl carbonate.

3-hydroxyesters and derivatives thereof produced from the carbonylation as described above are usually present in a concentration of 5~95 wt % of the total reaction mixture, which are represented by the following Formulas (VIII) or (IX):

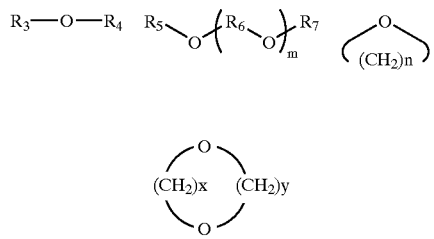

wherein,
each of $R_1$, $R_2$ and R' has, independently, the same meaning as defined above.

These compounds represented by the above Formulas (VIII) or (IX) have bifunctionality, so that they can be directly used as an intermediate for various organic syntheses or as a coating material. Additionally, these 3-hydroxyester compounds can be further converted into any other valuable compounds through diverse reaction pathways familiar with those skilled in the art as needed.

The present invention is characterized in that the final reaction product obtained from the carbonylation as described above as well as the reaction solvent used in the carbonylation are separated from the catalytic components (as used herein, by "catalytic components" are referred to the cobalt catalyst plus the promoter) in a stripping column by the use of a stabilizing gas. As used herein, by "stabilizing gas" is referred to any substance which does not react with 3-hydroxyesters and is present in a gaseous state at the temperature where such separation occurs and which shows beneficial effect to stabilize the catalytic components. Preferred stabilizing gases can be exemplified by carbon monoxide, nitrogen, helium, hydrogen, carbon dioxide, argon, neon, xenon, and mixtures thereof.

In the present invention, the choice of stabilizing gas and flow rate thereof, temperature of the stripping column, as well as inner diameter and length of the stripping column depends on which 3-hydroxyester compound to be separated. Temperature of the stripping column is controlled in the range of −30~200° C., preferably 0~150° C., and more preferably 10~120° C. Conventionally, when a compound is to be separated at a temperature lower than its boiling point, vacuum distillation technique has been used. However, the present inventors succeeded in separating the desired reaction product, 3-hydroxyesters, more efficiently at a temperature below the boiling point thereof utilizing a stripping system, which can operate in a non-vacuum condition at a low temperature and thus makes the separation process more economical.

Typically, the stripping column has a cylinder-like shape. Supposing that they have the same volume, a stripping column with smaller inner diameter and longer length is advantageous over that with larger inner diameter and shorter length in the light of separation efficiency. In the desired reaction product plus the solvent separated according to the subject technique, cobalt is present in a concentration of 10 ppm or less, so that it is desirable for the recovery of cobalt.

Specifically, the separation by a stripping column has a lot of advantages over either the extraction with an additional extraction solvent such as water or the vacuum distillation as follows:

First, the use of additional extraction solvent is likely to cause a rise in production cost due to the necessity for the recovery of the extraction solvent in a separate step following the separation of desired product, as well as side-reactions due to the separation solvent. In contrast, the use of a gas as in the present invention allows very easier separation of desired product by virtue of a large difference in boiling point and the suppression of any side-reactions.

Further, the separation of desired product by the conventional vacuum distillation incurs considerable cost for establishing vacuum distillation devices and maintaining vacuum condition, and there is also anxiety about a large-scale exposure of the product mixture when running commercial-scale vacuum distillation equipments at a vacuum condition. Advantageously, the separation in a stripping column with a gas as in the present invention minimizes the possibility for the product mixture to contact with outer atmosphere, because the separation is conducted under a positive pressure by the gas. In particular, the cobalt catalyst used in the present invention is very sensitive to air (or oxygen) and so the incidental contact with air (or oxygen) results in the significant reduction of catalytic activity. Therefore, by conducting the separation in a stripping column with an oxygen-free gas can be prevented such reduction of catalytic activity of the cobalt catalyst, because the exposure to air can be prevented. Furthermore, the separation of catalyst can be accomplished at a lower temperature than in the vacuum distillation, which also contributes to the preservation of the catalytic activity. Finally, almost complete separation of the catalytic components from the desired product can be achieved, which makes the recovery of cobalt easy regardless of the recycling of cobalt for the future use.

The product thus separated in a stripping column can be converted into 1,3-alkanediols through hydrogenation or can be converted into malonate or β-ketoester derivatives by oxidation. All or a part of the catalytic components (cobalt+promoter) can be recycled to the carbonylation reaction for continuous preparation of 3-hydroxyesters.

FIG. 1 illustrates an example of preparation of 3-hydroxyesters according to the present invention. In the reactor 5, epoxide 3 is reacted with carbon monoxide 1 and alcohol 2 in the presence of the catalytic components 4 (a catalytic amount of a cobalt compound plus an effective amount of a promoter) at a temperature of 30~150° C. under a pressure of 50~3000 psig optionally by using an additional solvent to afford a 3-hydroxyester or derivatives thereof.

Typically, only one reactor or several reactors arranged in a row are employed depending on the desired yield of 3-hydroxyesters, while the additional reactors 6, 7 may be connected to the rector 5 in a series as shown in FIG. 1. In this case, the reaction mixture in the rector 5 is transported to the rector 6 followed by the introduction of the additional reactants 1, 2 and 3 for further carbonylation to be continued, and then the reaction mixture in the rector 6 is transported to the rector 7 and subjected to further carbonylation in the similar manner. Likewise, additional reactors may be connected to the reactor 7.

At the completion of the reaction in the reactor 7, the reaction mixture 11 comprising reaction product, solvent, and catalytic components flows into the stripping column 12, in which the reaction product 15, the remaining reactant(s) 16 and the catalytic components(cobalt+promoter) 13 are separated from one another by using the stabilizing gas 14 at a temperature of −30~200° C. Catalytic components (cobalt-promoter complex) 13 thus separated are partially or fully recycled into the reactor 5 for use in the next carbonylation reaction. Meanwhile, the solvent may be isolated from the catalytic components 13 together with the reaction product and then be applied to the subsequent hydrogenation step. Alternatively, the solvent may be completely separated and recovered from the reaction product in an additional separation step (for example, by vacuum distillation) following the process in the stripping column, so that the solvent may be directly applied to the subsequent hydrogenation step together with the reaction product or be recycled to the previous carbonylation step.

The present invention can be more clearly understood with referring to the following examples. It should be understood that the following examples are not intended to restrict the scope of the present invention in any manner.

EXAMPLES 1 TO 5

Under nitrogen atmosphere, to a high-pressure Parr reactor at room temperature were added 200 ml of methanol and a catalyst consisting of $Co_2(CO)_8$ containing 6.8 mmol of cobalt and an imidazole compound (cobalt:imidazole=1:2 (mol/mol)). Into the reactor was flowed CO gas to 500 psig, and temperature of the reactor was elevated to 80° C. Then, the reaction mixture was stirred at that temperature for 1 hour, followed by addition of 1.36 mol of ethylene oxide and filling of CO gas to the limit of 85 atm. The reaction was continued for further 2 hours with maintaining the reaction temperature at 80° C. (Example 1).

In the Example 2, the reaction mixture obtained from the Example 1 was introduced into a stripping column (length: 60 cm; inner diameter 2.5 cm) at 60° C., and then heated at the same temperature for 2 hours with flowing CO gas up to down at the flow rate of 5 L/min to separate catalyst, reaction product and solvent. 20% of the catalyst thus separated was replaced with fresh catalyst containing 1.36 mmol of cobalt. This catalyst was then introduced to the reactor again and the overall reaction procedures were repeated as in the Example 1.

In the Examples 3~5, the same procedures as in the Example 2 were further repeated using the catalyst recovered from the former Example as many times as described in the column 2 in the following Table 2.

For the respective Examples, the reaction mixture was sampled after completion of the reaction and subjected to GC analysis for the final product. The results are summarized in the following Table 1 and FIG. 2.

TABLE 1

| Exam. | The number of times of catalyst recycling | Conversion rate (%) | Selectivity (mol %) | | | | | |
|---|---|---|---|---|---|---|---|---|
| | | | DMA[1] | AA[2] | HPM[3] | ME[4] | Dimer[5] | DD[6] |
| 1 | 0 | 83.2 | 0.3 | 9.1 | 74.9 | 2.8 | 11.2 | 0 |
| 2 | 1 | 78.7 | 0.5 | 6.7 | 76.2 | 3.3 | 9.3 | 0 |
| 3 | 2 | 80.0 | 0.4 | 6.0 | 72.1 | 3.5 | 12.1 | 0 |
| 4 | 3 | 79.4 | 0.4 | 5.6 | 69.5 | 3.6 | 13.1 | 0 |
| 5 | 4 | 80.9 | 0.1 | 5.9 | 65.8 | 3.4 | 15.9 | 0 |

[1] DMA: acetaldehyde dimethyl acetal
[2] AA: acetaldehyde
[3] HPM: 3-hydroxy propionic methyl ester
[4] ME: methoxy ethanol
[5] Dimer: $HOCH_2CH_2C(O)OCH_2CH_2C(O)OCH_3$
[6] DD(Dehydrated dimer): $CH_2CHC(O)CH_2CH_2(O)OCH_3$
Note)
Any other components than the above listed components exist as a mixture of unidentified compounds by the conventional GC-MS technique.

Figure 2:
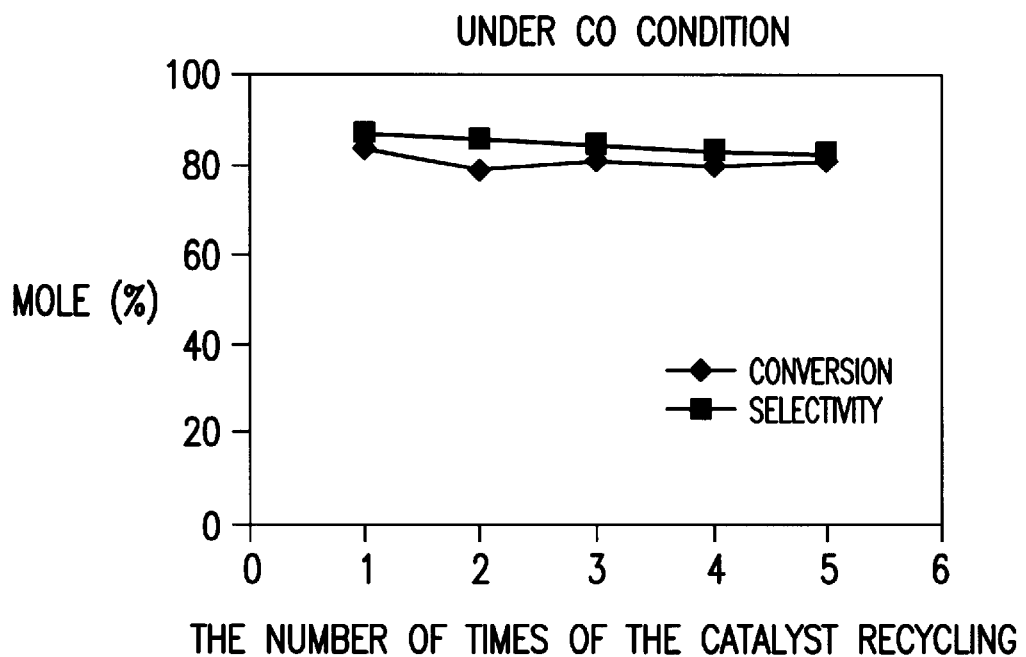
FIG. 2 is a graph showing the variation of conversion rate and selectivity in the case of recycling the catalyst isolated in a stripping column under CO condition according to Examples 1 to 5.
Figure 3:
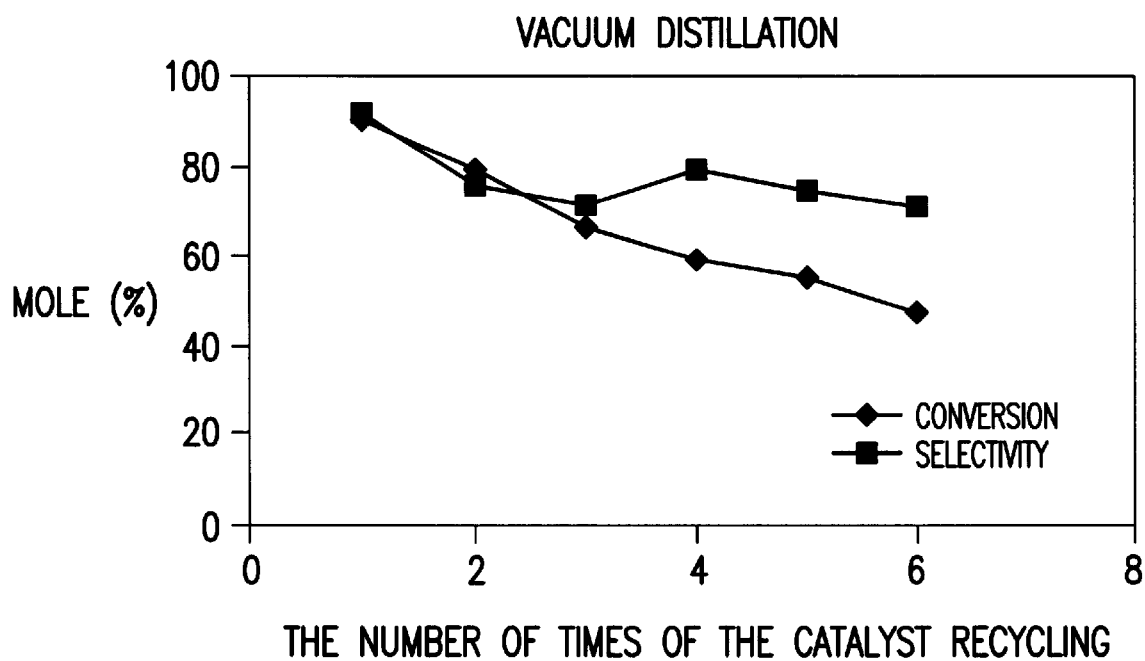
FIG. 3 is a graph showing the variation of conversion rate and selectivity in the case of recycling the catalyst isolated by vacuum distillation according to Comparative Examples 1 to 6.

In FIG. 2, the selectivity for HPM represents the sum of that for HPM and that for dimer. This is applicable to FIGS. 3–5.

COMPARATIVE EXAMPLES 1 TO 6

The separation of the catalyst from the reaction mixture was conducted according to the vacuum distillation technique which had been previously disclosed in the present inventor's Korean Patent Application No. 2001-1784. The catalyst was the same as used in the Example 1, and detailed reaction conditions are described below.

Analysis of the reaction mixture was conducted by GC analysis as in the above Examples 1 to 5. The results are summarized in the following Table 2 and FIG. 3.

As shown in the above Table 2, as the number of times of the catalyst recycling increases, the conversion rate is drastically decreased, and the selectivity for HPM varies severely.

EXAMPLES 6 TO 10

The procedure of Example 6 was conducted according to the same manner as in the above Example 1, and the procedure of Example 7 was conducted according to the same manner as in the above Example 2, except that $N_2$ gas was substituted for CO gas in the catalyst separation step from the reaction mixture obtained from the Example 6. In the Examples 8~10, the same procedures as in the Example 7 were further repeated using the catalyst recovered from the

TABLE 2

| Comp. Exam. | The number of times of the catalyst recycling | Conversion rate (%) | Selectivity (mol %) | | | | | |
|---|---|---|---|---|---|---|---|---|
| | | | DMA | AA | HPM | ME | Dimer | DD |
| 1 | 0 | 90 | 0.6 | 7.3 | 77 | 0 | 14 | 0 |
| 2 | 1 | 79 | 0 | 1.4 | 71 | 2.3 | 4.9 | 0.2 |
| 3 | 2 | 67 | 0 | 1.1 | 53 | 1.4 | 18 | 3.2 |
| 4 | 3 | 59 | 0 | 0.9 | 56 | 1.5 | 23 | 5.4 |
| 5 | 4 | 55 | 0.3 | 0.5 | 55 | 2.0 | 20 | 6.3 |
| 6 | 5 | 48 | 0.1 | 2.0 | 50 | 1.8 | 21 | 7.8 |

Note)
Tetraethylene glycol dimethyl ether = 100 ml;
Methanol = 100 ml;
$Co_2(CO)_8$ = 15 mmol;
Imidazole = 30 mmol;
Ethylene oxide = 1.5 mol;
Reaction temperature = 80° C.;
CO Pressure = 70 atm;
Reaction time = 2 hours;
Catalyst recycling time = 1 hour;
Vacuum distillation temperature = 50° C.;
Recycling temperature = 80° C.;
$CO/H_2$ = 2/1;
Pressure = 100 bar former Example as many times as described in the column 2 in the following Table 3.

Figure 4:
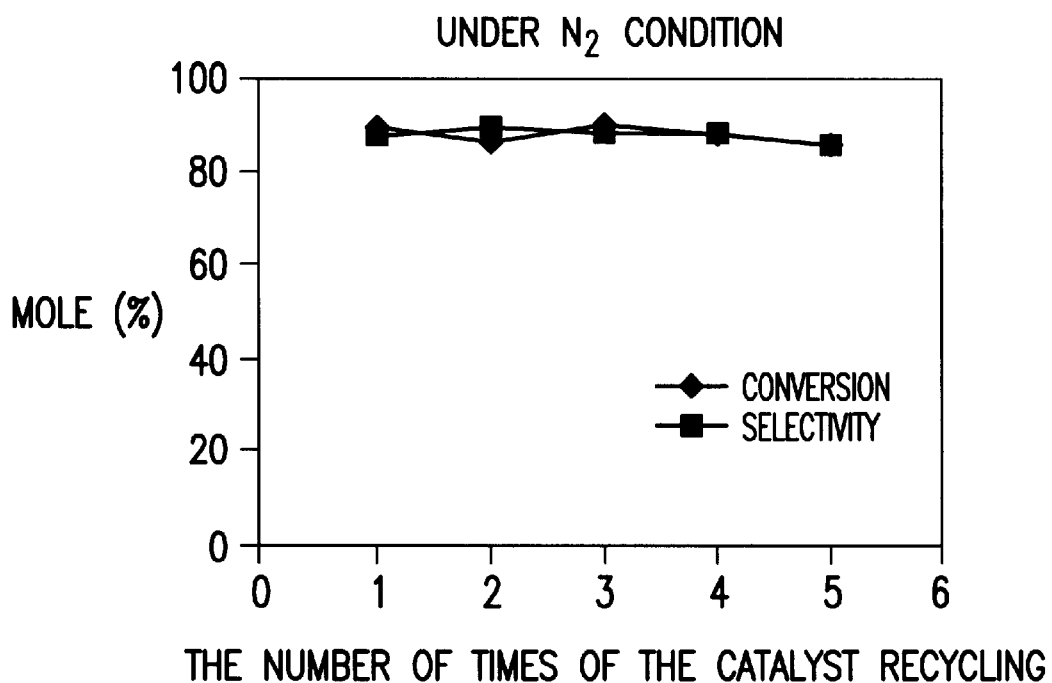
FIG. 4 is a graph showing the variation of conversion rate and selectivity in the case of recycling the catalyst isolated in a stripping column under $N_2$ condition according to Examples 6 to 10.

The results from GC analysis of the reaction products are summarized in the following Table 3 and FIG. 4.

TABLE 3

| Exam. | The number of times of the catalyst recycling | Conversion rate (%) | Selectivity (mol %) | | | | | |
|---|---|---|---|---|---|---|---|---|
| | | | DMA | AA | HPM | ME | Dimer | DD |
| 6 | 0 | 88.8 | 0 | 2.2 | 79.8 | 0 | 7.7 | 0.3 |
| 7 | 1 | 86.1 | 0 | 2.0 | 71.1 | 0.8 | 17.8 | 0.3 |
| 8 | 2 | 90.1 | 0 | 2.5 | 68.2 | 0.3 | 19.9 | 0 |
| 9 | 3 | 87.5 | 0.1 | 2.3 | 69.1 | 0 | 18.6 | 0 |
| 10 | 4 | 85.0 | 0 | 2.4 | 70.2 | 0 | 15.3 | 0 |

EXAMPLES 11 TO 13

The procedure of Example 11 was conducted according to the same manner as in the above Example 1, and the procedure of Example 12 was conducted according to the same manner as in the above Example 2, except that $H_2$ gas was substituted for CO gas in the catalyst separation step from the reaction mixture obtained from the Example 11. In the Example 13, the same procedures as in the Example 12 were further repeated using the catalyst recovered from the former Example as many times as described in the column 2 in the following Table 4.

Figure 5:
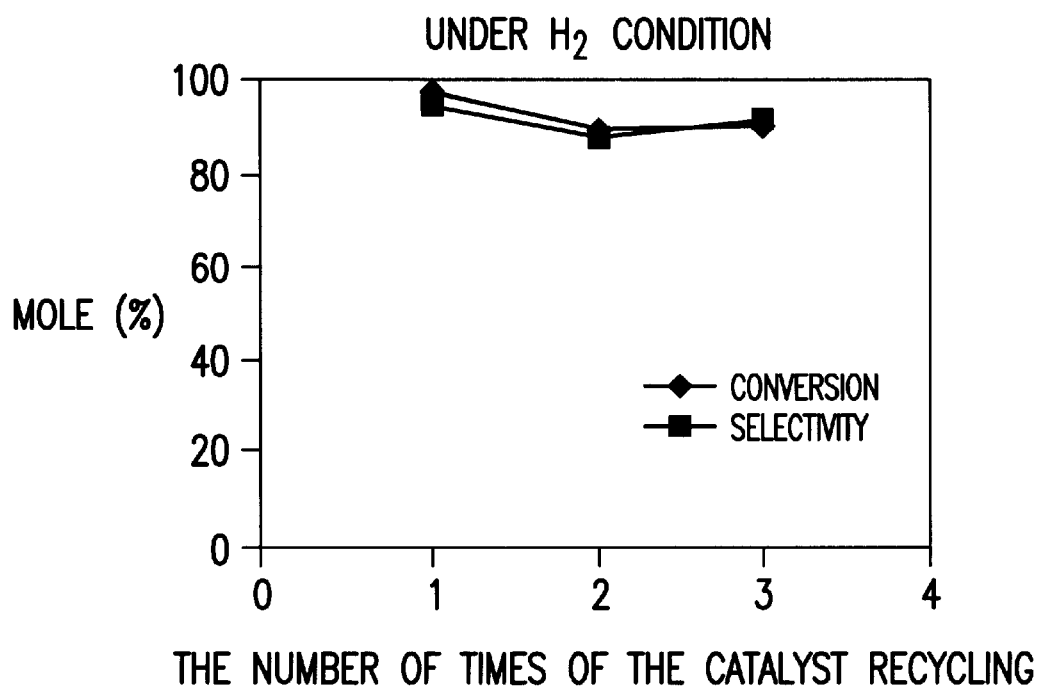
FIG. 5 is a graph showing the variation of conversion rate and selectivity in the case of recycling the catalyst isolated in a stripping column under $H_2$ condition according to Examples 11 to 13.

The results from GC analysis of the reaction products are summarized in the following Table 4 and FIG. 5.

TABLE 4

| Exam. | The number of times of the catalyst recycling | Conversion rate (%) | Selectivity (mol %) | | | | | |
|---|---|---|---|---|---|---|---|---|
| | | | DMA[1] | AA[2] | HPM[3] | ME[4] | Dimer[5] | DD[6] |
| 11 | 0 | 98.0 | 0 | 5.0 | 91.9 | 0 | 3.1 | 0 |
| 12 | 1 | 89.7 | 0 | 1.9 | 77.3 | 1.0 | 11.2 | 0.9 |
| 13 | 2 | 91.0 | 0 | 2.0 | 79.5 | 0.6 | 12.0 | 0.5 |

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A process for preparing 3-hydroxyesters, comprising:

(a) reacting an epoxide derivative with carbon monoxide and alcohol in a solvent at a temperature of 30~150° C. under a pressure of 50~3000 psig by using a catalyst system consisting of a catalytic amount of a cobalt compound and optionally an effective amount of a promoter to produce a 3-hydroxyester or a derivative thereof;

(b) separating the resulting product and the solvent from the cobalt compound and the promoter in a stripping column at a temperature of −30~200° C. in an atmosphere of a stabilizing gas; and (c) recycling a part or all of the separated cobalt compound and promoter to the step (a) and repeating the steps (a) through (c).

2. The process according to claim 1, the catalyst system is a cobalt catalyst $Co_2(CO)_8$ alone, or the cobalt catalyst $Co_2(CO)_8$ in combination with a promoter selected from the group consisting of imidazole, pyridine, pyrrole, pyrazine, pyrazole, pyrimidine, piperidine and derivatives thereof.

3. The process according to claim 1, wherein molar ratio of cobalt atom:promoter in the catalyst system is in the range of 1:0 to 1:100(mol/mol).

4. The process according to claim 1, wherein the promoter is imidazole derivatives represented by the following Formula (I):

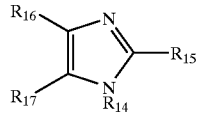

wherein,
each of $R_{14}$, $R_{15}$, $R_{16}$ and $R_{17}$ is, independently, hydrogen; $C_{1-10}$ branched aliphatic hydrocarbon, non-branched aliphatic hydrocarbon, saturated cyclic hydrocarbon, chain-type hydrocarbon containing ring structure, or aliphatic hydrocarbon containing aromatic ring; F; Cl; $C_{1-3}$ alkoxy group; OH; or OH-containing $C_{1-10}$ branched aliphatic hydrocarbon, non-branched aliphatic hydrocarbon, saturated cyclic hydrocarbon, chain-type hydrocarbon containing ring structure, or aliphatic hydrocarbon containing aromatic ring.

5. The process according to claim 4, wherein the promoter is imidazole.

6. The process according to claim 1, wherein the epoxide derivative is represented by the following Formula (II):

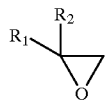

wherein, each of $R_1$ and $R_2$ is, independently, hydrogen; $C_{1-20}$ saturated non-branched aliphatic hydrocarbon, branched aliphatic hydrocarbon, saturated cyclic hydrocarbon, chain-type hydrocarbon containing ring structure, or aliphatic hydrocarbon containing aromatic ring; hydrocarbon formed by substitution of at least one hydrogen in at least one carbon chain of the above hydrocarbon species with F, Cl or Br; unsubstituted aromatic hydrocarbon; or aromatic hydrocarbon formed by substitution of at least one hydrogen in the aromatic ring with F, Cl, amine, nitrile or alkoxy group.

7. The process according to claim 1, wherein the solvent is an ether compound, a substituted aromatic compound, an acetate compound, a carbonate compound, or an alcohol.

8. The process according to claim 1, wherein the stabilizing gas is carbon monoxide, nitrogen, helium, hydrogen, carbon dioxide, argon, neon, xenon, or a mixture thereof.

* * * * *